United States Patent [19]

Woodward

[11] Patent Number: 4,821,215

[45] Date of Patent: Apr. 11, 1989

[54] MONITORING EQUIPMENT FOR ADVERSE ENVIRONMENTS

[75] Inventor: Steven J. Woodward, Port Hope, Canada

[73] Assignee: Canadian Corporate Management Company Limited, Peterborough, Canada

[21] Appl. No.: 916,013

[22] Filed: Oct. 3, 1986

[51] Int. Cl.[4] .................. G01S 15/46; G06F 15/74
[52] U.S. Cl. .................. 364/550; 340/815.31; 73/620; 364/561; 364/571.03; 367/908
[58] Field of Search ............... 364/550, 551, 561, 562, 364/564, 571; 73/29, 620; 340/815.31; 455/603; 366/21; 367/99, 908

[56] References Cited

U.S. PATENT DOCUMENTS

| | | | |
|---|---|---|---|
| 4,330,174 | 5/1982 | Douglass et al. | 340/815.31 X |
| 4,436,431 | 3/1984 | Strong et al. | 366/21 |
| 4,596,144 | 6/1986 | Panton et al. | 73/620 |
| 4,675,854 | 6/1987 | Lau | 367/908 |
| 4,700,569 | 10/1987 | Michalski et al. | 73/290 V |
| 4,703,359 | 10/1987 | Rumbolt et al. | 455/603 X |

FOREIGN PATENT DOCUMENTS

| | | | |
|---|---|---|---|
| 142394 | 5/1985 | European Pat. Off. | 364/465 |
| 180423 | 5/1986 | European Pat. Off. | 455/603 |

Primary Examiner—Felix D. Gruber
Attorney, Agent, or Firm—Ridout & Maybee

[57] ABSTRACT

Programmable apparatus for monitoring an industrial installation, such as for measuring the depth of material in bins or silos, utilizes a computer having a hermetically sealed case, with an externally visible display and necessary connections to the installation being monitored. The computer includes non-volatile random access memory for the storage of operating parameters which is written to under control of a portable external programming unit which can temporarily access the computer via an infrared or equivalent communications link. The case of the computer has provision for temporary docking of the programming unit, which has a keypad for the selection of calibration and diagnostic routines, and the entry of data or commands to be transmitted to the computer.

6 Claims, 6 Drawing Sheets

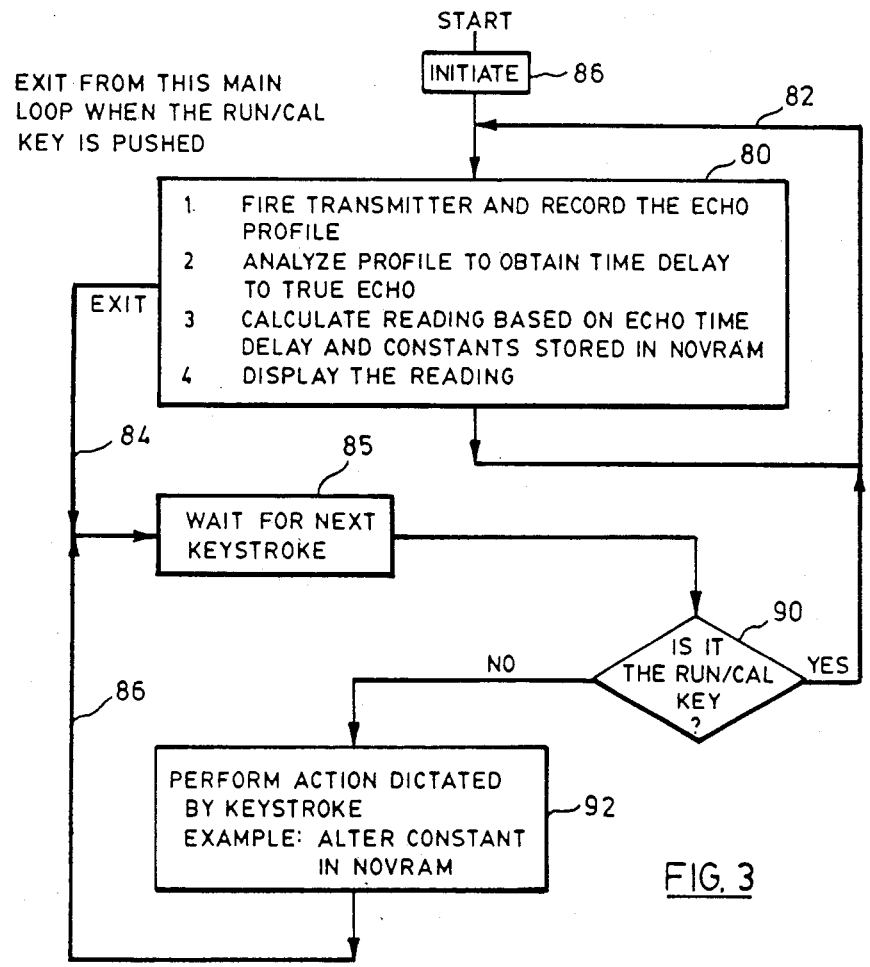

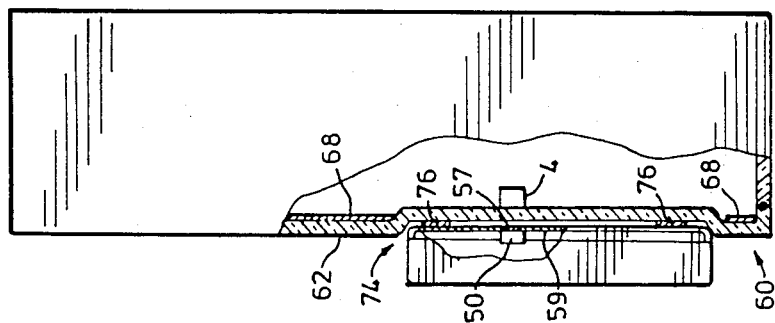
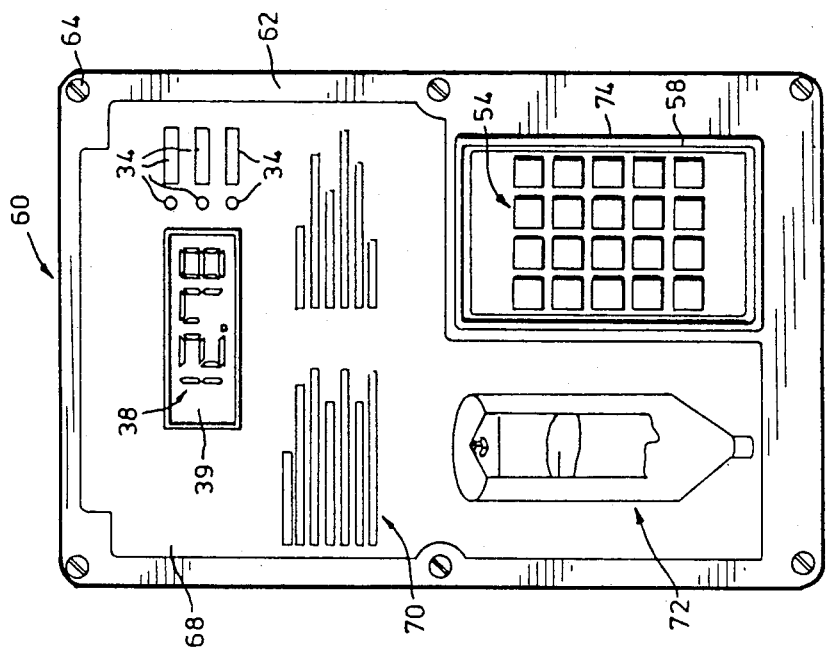

MONITORING EQUIPMENT FOR ADVERSE ENVIRONMENTS

FIELD OF THE INVENTION

This invention relates to process control equipment for use in adverse environments, and particularly although not exclusively to measuring depths of solids and liquids in containers and channels.

BACKGROUND OF THE INVENTION

In recent years, wide use has been made of microprocessor based process control units for supervising industrial operations. Examples of such operations are the monitoring of the depth of material in silos and bins, the depth of fluid in channels, and the rate of flow of materials on conveyor belts. Typically, such equipment incorporates inputs from one or more transducers, connections to alarm or recording devices, and an operator interface consisting of some form of visual read out and some form of data entry keyboard which can be utilized for entering data into the unit. Electronically, the unit comprises a microprocessor associated with read only and random access memory and suitable peripheral interfaces so as to form a dedicated computer.

Such a unit most commonly operates under very adverse conditions in terms of the presence of dust, dirt, moisture and rough handling, and at the same time is also usually required to maintain calibration within fairly narrow limits. In this connection, the provisions for data entry in conventional units are a weak point, both since keyboards are vulnerable to the adverse conditions mentioned above, and because they may provide a means for unauthorized or inadvertent reprogramming or recalibration of the unit. Clearly there are measures which can be taken to alleviate these problems, but they increase the cost and complexity of the unit and its programming.

An example of a process control unit of the general class discussed above is described in U.S. Pat. No. 4,596,144 (Stanley Panton and Steven J. Woodward) entitled "Acoustic Ranging System", the specification of which is incorporated herein by reference. Reference to FIG. 1 of the drawings of that patent will show that it incorporates a computer 28 provided with various connections to transducers, indicators and displays, and receiving inputs from a keyboard 52 and control keys 58.

It has been proposed to connect the keyboard of a personal computer to the main unit of the computer by an infrared link. Such an arrangement was for example used in the IBM PC JR. (Trade Mark) computer. Numerous applications are also known in which portable keypads are utilized to provide remote control of domestic equipment such as television sets again using an infrared or ultrasonic link, although in the latter case, provision is invariably made for additional local control of the appliance.

SUMMARY OF THE INVENTION

The present invention in a first aspect seeks to provide an improved unit for monitoring functions in an industrial installation, which is environmentally sealed, and requires no keyboard or other directly human accessible data entry device, whilst still permitting authorized amendment of the parameters of the monitoring function.

Accordingly the invention provides a unit providing at least one monitoring function for an industrial installation comprising an environmentally sealed casing, said casing having sealed window means providing the sole direct user interface to the unit, and containing a computer comprising a microprocessor, a read only memory accessible by the microprocessor and containing a stored program dedicating the microprocessor to at least one predetermined monitoring function, a human readable visual data display device within the casing and visible through said window means, a radiation transducer within the casing and responsive to data modulated radiation of a type to which at least part of the casing is transparent, at least one first peripheral interface element and second and third peripheral interface elements, said first, second and third peripheral interface elements interfacing the microprocessor respectively to connections for at least one monitoring transducer external of the casing and associated with said installation, to said data display device, and to said radiation transducer, a first random access memory accessible to the microprocessor and providing working memory and temporary data storage therefor, a second non-volatile random access memory accessible to the microprocessor and providing storage for data relating to normally constant parameters of said at least one monitoring function, said stored program consisting of a first normally active portion configuring the computer to carry out the at least one monitoring function of the unit, said portion accessing said second memory only for the reading of said normally constant parameters from defined locations therein, and a second normally inactive portion operative to decode signals received from the radiation transducer by the third peripheral interface unit to recover data representing said normally constant parameters, and to store said data in said defined locations in said second memory responsive to said signals, the third peripheral interface element including means responsive to receipt of signals from the radiation transducer to activate said second program portion.

The invention also extends to an improved method of acoustic ranging having improved immunity to adverse environmental conditions.

The invention is described further with reference to the accompanying drawings, in which:

IN THE DRAWINGS:

FIG. 2 is a schematic diagram of a calibrator unit for use with the system of FIG. 1;

FIG. 3 is a flow diagram outlining the programming of the system of FIG. 1;

FIG. 4 is a diagrammatic front view illustrating the interaction of the calibrator with a system unit;

FIG. 5 is a fragmentary vertical section through part of the calibrator and system unit;

DESCRIPTION OF THE PREFERRED EMBODIMENTS

Figure 1:
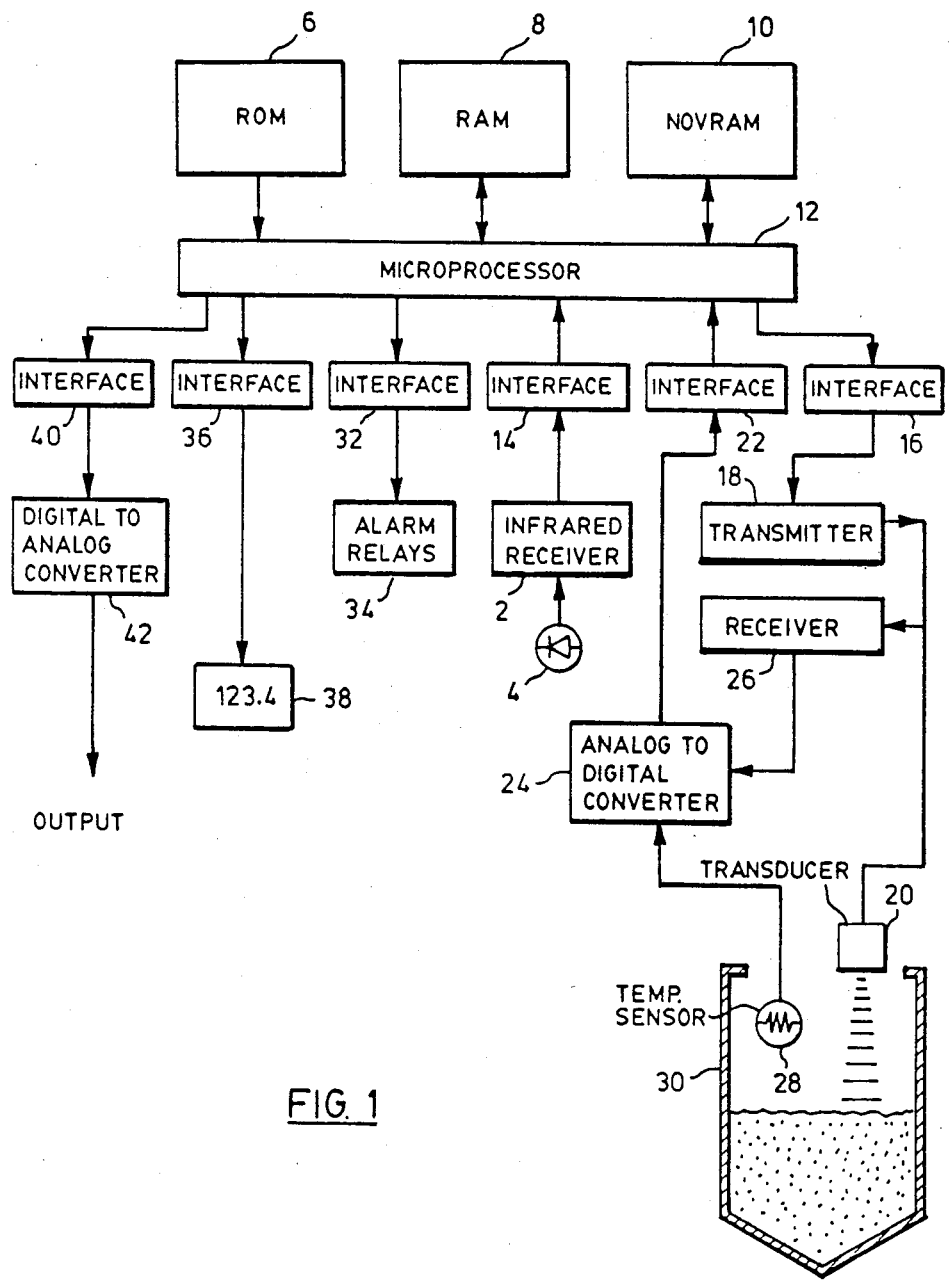
FIG. 1 is a schematic diagram of the principal components of a level monitoring system incorporating the invention.

Referring to FIG. 1, the diagram shown of a computer unit is a simplified version of that shown in FIG. 1 of U.S. Pat. No. 4,596,144, with the difference that the keyboard 52 and control keys 58 of that patent are replaced by an infrared receiver 2 associated with an infrared sensor diode 4, and the division of the memory in three rather than two parts, read only memory 6, random access memory 8 and non-volatile memory 10. The non-volatile memory may be implemented by a conventional RAM with battery backup, or implemented by RAM chips with integral battery backup, or by electrically alterable and erasable read only memory, or magnetic bubble memory or any other suitable technology combining the ability to retain memory content under power down conditions with the ability to alter memory content under program control. The non-volatile memory, referred to for convenience as NOVRAM, is utilized for retaining constants which are dependent on a particular installation or configuration or which only require alteration at long intervals, such as configuration and calibration data.

The read only memory 6 contains a predetermined program which controls a microprocessor 12, which in turn utilizes the random access memory 8 for working memory and temporary storage of variable data, whilst constants other than those predetermined by the program itself are stored in the NOVRAM 10. The main portion of the program itself, the relevant features of which are outlined in FIG. 3, may be essentially as described in U.S. Pat. No. 4,596,144 except for amendment to segregate the data addresses utilized appropriately between the memories 8 and 10, and any revision of the routines associated with an interface 14 to the receiver 2 so as to suit it to receive data from such a source rather than a keyboard or control keys. The program is preferably further developed as set forth below with reference to FIG. 6, so as to further improve performance under adverse conditions.

Further interfaces are provided to various other microprocessor peripherals. An interface 16 is provided to a transmitter 18 sending pulses to an external ultrasonic transducer 20, and interface 22 with an analog to digital converter 24 receiving return signals from the transducer 20 via a receiver 26, and from an external temperature sensor 28. The transducer 20 and sensor 28 are appropriately mounted in relation to a bin or silo 30 which is being monitored. An interface 32 is provided to an alarm relay unit 34, which may drive alarm indicator lamps 36 (see FIG. 4) and possible external alarm devices, whilst an interface 36 drives a digital display 38. A further interface 40 drives a digital to analog converter and current source serial data transmitter 42. Whilst the various interfaces have been shown as separate functional blocks, it will be understood that they may be implemented by a lesser number of physical interface circuits providing multiple ports, or may be integrated either into the peripheral circuit which they interface or into a microcomputer which may incorporate the microprocessor 12 and all or part of the memories 6 and 8.

The diode 4 associated with the receiver 2 can receive modulated data from infrared source diode 50 driven by a coding circuit 52, which causes the diode 50 to emit different pulse trains according to which key of a number of keys, typically about 20 on a keypad 54 has been depressed. The diode 50, encoder 52, a battery 56 powering the circuit 52, and the keypad 54, are incorporated into a small portable calibrator unit 58 (see FIG. 4) which may be constructed similarly and utilizing similar devices, to the infrared remote control units widely used to control domestic appliances such as television sets. It should be understood however, as discussed further below, that the unit is not utilized as a remote control unit in the usual sense. The receiver 2 and diode 4 may also be similar to those utilized in remote control receivers and providing digital outputs responsive to key presses applied to a keypad on a transmitter.

Referring to FIGS. 4 and 5, the components of the computer described with reference to FIG. 1, apart from those described as "external" such as the transducer 20, the sensor 28, any external alarms, and the destination of the current source output 44 from the block 42, are housed within a case 60 together with a suitable power supply (not shown). Typically the case 60 is of die cast construction with a die cast front cover 62 secured to the casing by screws 64 and sealed to it by an O-ring 66. The material from which the case is cast may be polycarbonate resin, which in the case of the front cover may be transparent, with an aluminum mask 68 attached to its inner surface, so as to leave transparent windows for the display 38, indicator lamps 34 and the diode 4, and to provide a protected surface for carrying user information such as a list 70 of operation parameters which can be altered, and a diagram 72 explaining some of those parameters.

The front cover is moulded with a rectangular recess 74 which provides a docking bay for the unit 58. The unit 58 has a steel case, or at least a steel back plate 59 so that it may be releasably detained in the docking bay by magnetic strips 76. The sensor diode 4 is mounted behind the recess at a window in the mask 68, and the source diode 50 is mounted in front of a window 57 in the back plate 59 so that it is aligned with the diode 4 when the unit 58 is docked in the recess 74, thus establishing an optical path between the diodes.

Operation of the microprocessor 12 is controlled by a program stored in ROM 6, a simplified flow diagram of this program being shown in FIG. 3. The program consists of a main program loop 82 through a main program 80, which represents the normal monitoring functions of the unit. In the example shown, this comprises:

(1) sending an instruction through the interface 16 to the transmitter 18 to apply a pulse to the transducer 20, and storing to RAM 8 the return signals picked up by the transducer 20, processed by the receiver 26 and digitized by the analog to digital converter 24;

(2) analyzing the profile to obtain and store in RAM 8 data representing the elapsed time from transmission of the pulse to receipt of a line echo, using for example one of the techniques set forth in U.S. Pat. No. 4,596,144, or that described with reference to FIG. 6;

(3) calculating data representing the level of material in the silo 30 based upon the elapsed time data and data stored in NOVRAM 10;

(4) displaying the level data on the display 38, as well as triggering appropriate alarm relay 34 in the event that the data is abnormal;

and looping back to step (1).

It will be understood that the above loop has been outlined merely for the sake of example, and could be replaced by any of the methods disclosed in U.S. Pat.

No. 4,596,144, or other alternative methods capable of being controlled by a repeatedly executed program loop, or by other such techniques appropriate to some other equipment being monitored. The loop may contain subsidiary loops. For example, if the equipment being monitored was a belt scale, the program might include an inner loop involving receipt of a trigger pulse from a tachometer generator, sensing and digitizing the output of load cells associated with the scale, and an outer loop integrating the digitized output signals and calculating, on the basis of constants stored in NOVRAM, the flow rate and/or total weight of material being conveyed. Moreover, this main program loop may include alternative subroutines which are selected on the basis of data stored in the NOVRAM 10, for example to carry out different alternative processing algorithms on the basis of the data captured, or to selected different data to display or different forms of data. The actual content of the main program loop may be varied to suit the application provided that the loop includes some safe point of exit and re-entry from the routines described below, although a preferred embodiment is described with reference to FIG. 6.

Under normal operating circumstances, the program will follow the main loop and provide a display as determined by the constants stored in NOVRAM 10, until caused to exit the loop at 84 by receipt by the interface 14 of a signal indicating that data is being received by the diode 4. Conveniently this is achieved by programming the interface 14, upon power up of the computer in an initiation step 86 and prior to entering the main program loop 82, to issue an interrupt to the microprocessor 12 in response to receipt of data from the receiver 2, causing the latter to enter an interrupt service routine.

Alternatively, the main program 80 may include a polling routine which periodically tests the interface 14 to determine whether it holds data and branch to an equivalent of the interrupt service routine. The service routine tests the data received to determine whether it is a valid signal to leave the main loop, and if it is so, causes execution to branch from a suitable exit point 84 to a secondary program loop 86. A suitable exit point will normally be on completion of a circuit of the main loop 87, and if this is likely to take appreciable time, the service routine may cause a message or acknowledgement to be displayed on display 38 pending completion of the loop. For example, the message may be CAL to indicate entry to a calibration mode, which message can be displayed using characters that can be displayed by a conventional seven-segment digital display. A valid signal to leave the main loop will typically be that received by receiver 2 in response to pressing of a particular key on the keypad 54 when the unit 58 is docked in the recess 74. In the example shown this key is selected to be RUN/CAL (run or calibrate) key 55.

Upon entering the secondary program loop 86, the next step 88 is to wait for data representing a further keystroke. On receipt of such data, a test is made at 90 to determine whether it represents the RUN/CAL key 55 or some other key. In the event that the RUN/CAL key has been pressed execution branches at 92 back to the re-entry point of the main program loop 82. The RUN/CAL key is thus utilized to toggle execution between the main and secondary program loops. Different keys or keystroke sequences could be utilized to achieve this toggling, but the technique described is simple both to use and to implement.

In the event that the next keystroke data received does not represent the RUN/CAL key 55, then execution loops through a secondary program 92 and back to step 88.

Typically, a primary function of the secondary program 92 is to examine and alter parameters in the form of constants which are stored in the NOVRAM 10 and utilized by the main program 80. In the example being considered, the secondary program operates to process successive key presses entered through the keypad 54 so as to result in codes being transmitted to the interface 14. Assuming that it has been decided in step 90 that the codes do not represent the RUN/CAL key, the code received is compared with successive codes to determine whether it is a function key, and if so which one, or a numeric key, and the program branches to different subroutines accordingly. The NOVRAM 10 is organized to provide storage for data representing a number of predeterminable parameters of the equipment being monitored, for example the dimensions of a silo being monitored, and high and low alarm levels, the manner in which data is to be presented, for example in metric or other units, whether various options are present or enabled, and whether or not to display values determined or determinable from values determined by the main program, but not normally displayed. Each such data item is allocated a parameter number which identifies the address in the NOVRAM of the data item concerned. Parameter numbers may also be utilized to identify certain test, diagnostic and calibration routines which it may be desired to select by means of the keypad, as described further below.

The secondary program presents two alternative classes of data to the display 38, firstly parameter numbers which are identified by the prefix P, and secondly data associated with those parameter numbers, and the program itself operates in two phases according to whether parameters are being selected or data displayed. In general, the program is toggled between these phases by detection of successive presses of the ALT DISP key 94. In the parameter selection phase, a parameter number is selected and displayed by selective use of the *, ↑, ↓ and numeric keys. Thus the * key for example causes selection of parameter 01 and display of the characters P-01, the ↑ and ↓ respectively increment or decrement the parameter number stored and displayed, and entry of a 2 digit (in this example) number causes selection and display of the corresponding parameter number if available. Once a desired parameter number has been selected, a press of the ALT DISP key 94 will cause the program to enter its second phase in which a routine is selected according to the parameter number selected. If the parameter number designates a constant held in NOVRAM, then a routine is called to display the value of that constant. When a constant is so displayed, detection of a press of the ↑ or ↓ key will result in execution being temporarily returned to the first phase of the program for selection and display of an incremented or decremented parameter number, followed by a return to display the data associated with the newly selected parameter. Detection of presses of numeric keys during display of a numeric constant will result in replacement of the displayed constant by the numerals keyed in, whereafter the keyed in value may either be cleared using the CLEAR key or entered using the ENTER key, in which case it will be stored in NOVRAM in replacement of the previously stored value.

It will be understood that by use of the keys in the manner outlined above, the parameters stored in NOVRAM 10 may be quickly and easily reviewed and modified. These parameters may include not merely numeric data concerning dimensions of apparatus being monitored, alarm thresholds and similar data, but may include data which is tested by the main program for example to determine which of several different data processing algorithms are to be utilized, or what class of data is to be displayed by the main program and in what form.

As mentioned above, some parameters do not identify data stored in NOVRAM, but instead are utilized to initiate test or diagnostic routines. For example, selection of a particular parameter may be arranged so that a press of the ENTER key calls a routine which pulses all of the segments of the display and the alarm relays on and off so as to verify their function.

Selected parameters may be utilized to access routines useful during set up and calibration. For example, U.S. Pat. No. 4,596,144 describes methods of detecting a true echo in an ultrasonic range finding system which are essentially of a statistical nature, and not only identify an echo resulting from a particular shot but are capable of quantifying the degree of assurance that a selected echo is a true echo. This latter information may be utilized in determining whether additional shots are required to provide reliable data. I have now determined however that this assurance factor can be very advantageously utilized to facilitate installation of ultrasonic range finding transducers. The sitting of such transducers in an installation to be monitored has hitherto called for considerable skill and experience combined with trial and error testing if good results are to be obtained. I have found that by entering a selected parameter to call a routine in the secondary program which calls a routine in the main program (such as that described below with reference to FIG. 6), to cause the transmitter to fire a single pulse and processing of the received signal to select the true echo and obtain the assurance factor that this is the correct echo, and which then displays the assurance factor, then by repeated entering of the parameter as the transducer is positioned, the latter may be located in the position which provides the highest assurance factor and thus the best chance of selecting the correct echo. It should be noted that this position will not necessarily be the position producing the strongest echo or highest transducer efficiency, since the strength of the true echo is less important than the ability of the signal processing circuit to isolate it from spurious echoes, which it may be possible to minimize by careful positioning of the transducers.

Figure 6:
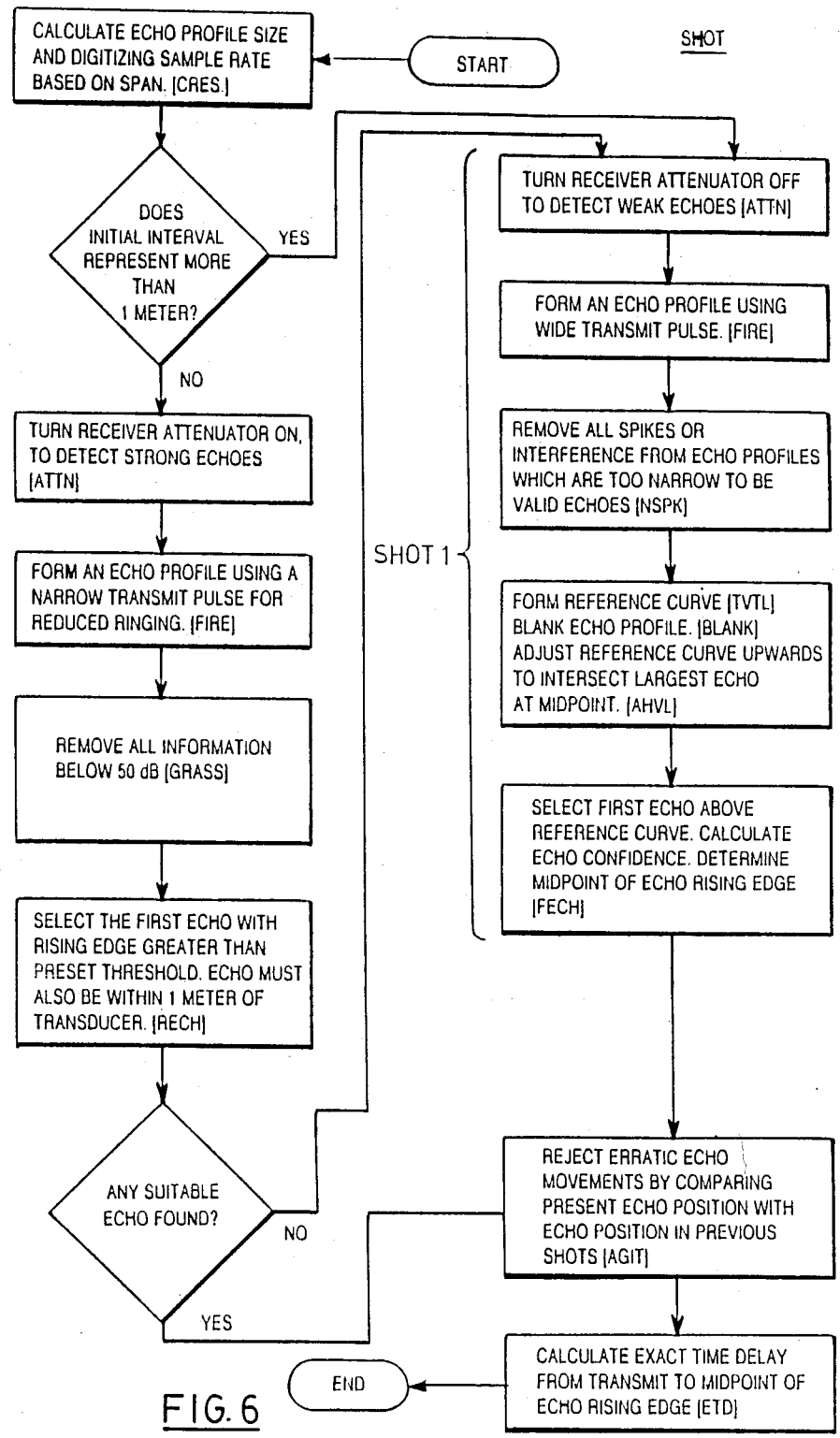
FIG. 6 is a flow diagram which shows in more detail the signal processing technique forming one step of a main program loop shown in FIG. 3.

Referring now to FIG. 6, a routine representing the preferred embodiment of step (2) of the main program 80 is shown in more detail; relevant portions of actual source code embodying the principal portions of the routine form the Appendix to this specification. The source code is written in assembly language for the Motorola 6809 microprocessor, utilizing mnemonics to represent operating and pseudo-operations in accordance with those published by Motorola for that microprocessor. To assist in following the source code, it should be noted that RAM 8 is located in low memory, and the ROM 6 in high memory. The interfaces to the various peripherals are also memory mapped, including the following; the interface 40 at hexadecimal 2000, the interface 22 at hexadecimal 4000, and the interface 14 at hexadecimal 7000. Parameters stored in NOVRAM or RAM are accessed and stored by routines RCL and STO, which together with other conventional subroutines such as display routines are not included in the Appendix.

The routine to be described has similarities to similar functions described in U.S. Pat. No. 4,596,144 and may be incorporated into the procedures described in that patent. It addresses itself however to an additional problem which frequently arises in practical installations.

All of the echo extraction techniques described in U.S. Pat. No. 4,596,144 have the following steps in common:

1. An echo profile is formed by taking one or more shots.
2. The first part of the echo profile is blanked in order to cover over the transmit pulse and some transducer ringing. Although the start of the echo profile coincides with the start of the transmit pulse, the useful information occurs after the end of blanking.
3. A reference curve is formed. The curve starts at a fixed start point and then follows the echo profile.
4. The most probably correct echo is selected by comparing the echo profile with the reference curve.

The problem arises in step 3. On the one hand it is desirable to set the start point low in order to confidently detect valid close in echoes. On the other hand it is desirable to set the start point high so that the reference curve will clear the unblanked portion of the transducer ringing, otherwise the ringing may be deemed to be the correct echo in step 4.

In the apparatus described in U.S. Pat. No. 4,596,144, the start point may be set manually by entering a value from the keyboard, or automatically. To set the start point automatically, the operator must first ensure that the material level is well down from the transducer, and then by use of the keyboard instructs the computer to calculate a start point which will cause the reference curve to clear the transducer ringing. The start point cannot be set with a full bin because the valid close in echo would appear to be transducer ringing and the start point would need to be set high to clear this echo.

A further problem arises because of variations in transducer ringing. The ringing may increase for the following reasons:

1. An increase or decrease in temperature.
2. A change in the mounting of the transducer; for example, the mounting bolts of the transducer may be tightened.
3. Natural aging of the transducer.
4. Replacement of the transducer.

The operator must recognize these factors and set the start point high enough to clear the worst case expected ringing. If the start point is too high then valid close in echoes will not be detected. If the start point is set too low then the apparatus may initially operate correctly, but a change of season will probably cause an increase in ringing and the start point must then be increased. If a compromise cannot be achieved then the blanking must be increased so that less of the ringing is seen. The disadvantage to increasing the blanking is that levels in the top portion of the bin cannot be measured, and the useful height of the bin is thus reduced.

In the transmitter design a trade off is made in selecting the transmit pulse width. A narrow pulse width has the effect of shifting the ringing to the left, when viewed graphically, simply because the end of transmission occurs sooner. The position of the echo remains the same and therefore close in echoes will stand out more above the ringing. A wide transmit pulse has the effect of producing the largest possible return echo, even in the presence of air currents which tend to disperse the sound wave, as often happens with distant targets.

Much effort has been directed to improving transducer performance, but in the present state of the art it is not possible to consistently manufacture a transducer with low and stable ringing while still maintaining other desirable features such as high sound output and rugged construction.

Although reliable operation throughout the full height of a bin is important, operation in the top region of the bin is frequently considered to be critical. A failure to indicate the correct level in the top region could result in the bin being overfilled. A solution to the problems described above would be highly desirable.

Objects of this aspect of the present invention thus include the ability to relieve an operator from any involvement in setting the start point or similar parameter, the ability to have the system continuously and automatically compensate for changes in transducer ringing, and the ability to automatically adjust the transmit pulse width so that close in echo detection is improved without compromising far echo detection.

The invention in this aspect provides a method of acoustic ranging in which a pulse of acoustic energy is transmitted from a transducer which is also utilized to receive an echo reflected from the surface of material whose level it is desired to detect, and in which a profile of the variation of the output of the transducer with time following the pulse is examined in order to detect the echo, the improvement wherein a profile is obtained using a narrow transmitted pulse, and a first portion of that profile is examined for the presence of the echo, and if no echo is detected in said first portion, a further profile is obtained using a broader transmitted pulse, a first portion of the echo profile is discarded, and the remainder is examined for the presence of an echo.

Figure 7A:
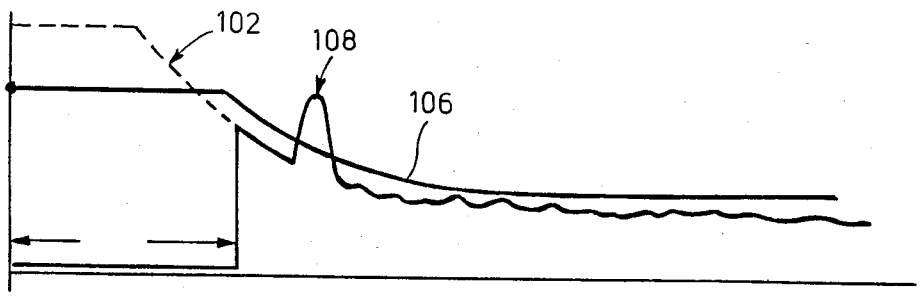
FIGS. 7a, 7b and 7c are graphs illustrating the problems which the signal processing technique is directed to tackling.
Figure 7B:
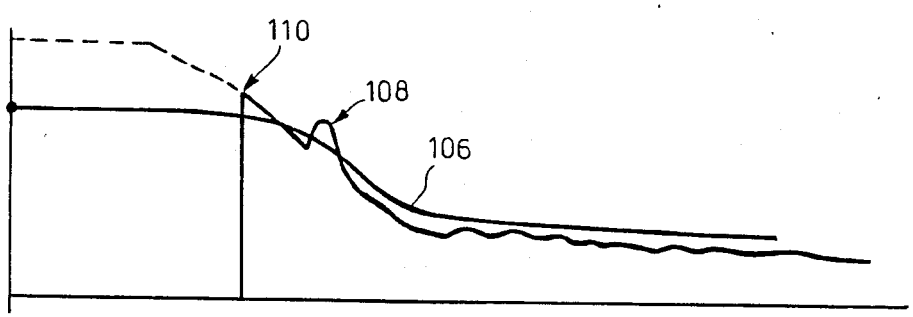
Figure 7C:
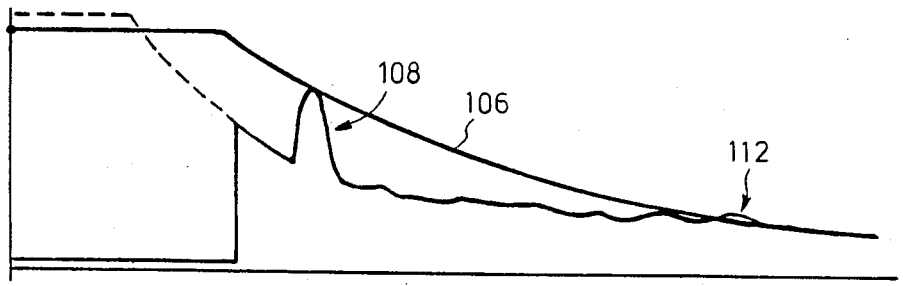
Figure 8A:
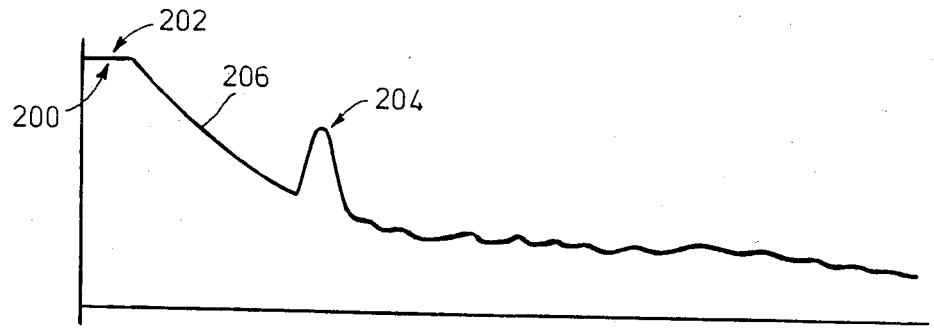
FIGS. 8a, 8b and 8c illustrate how these problems are tackled.
Figure 8B:
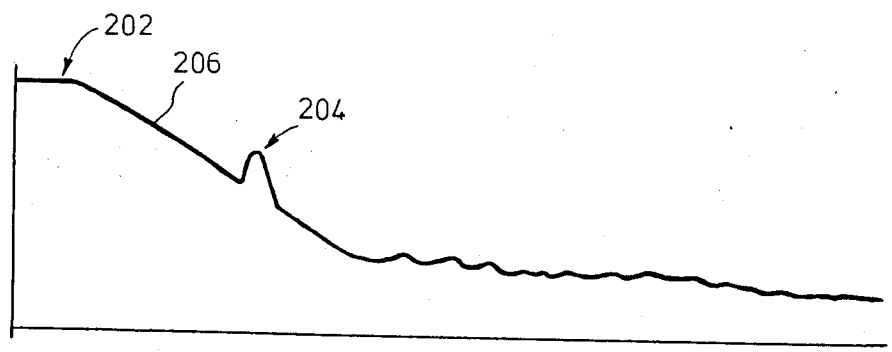
Figure 8C:
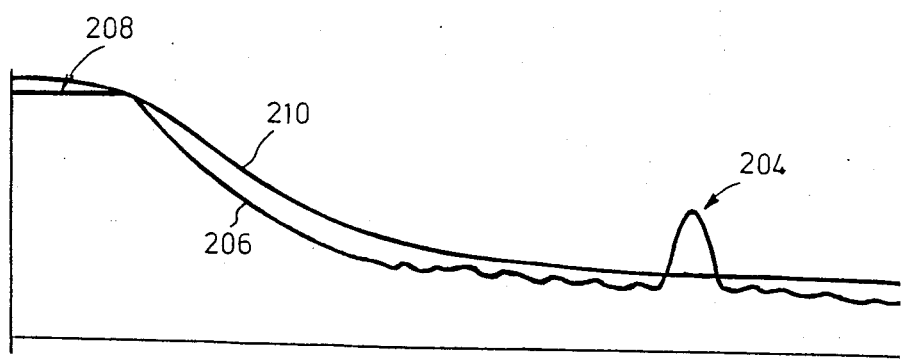

Referring to FIG. 7a, conventional systems of the above type utilize blanking 100 to discard the first portion 102 of the received echo profile 104, so as to eliminate that portion of the response where the amplitude of the response due to transducer ringing is still very high, and so would otherwise intersect the reference curve 106 utilized to detect a wanted echo 108. If the ringing level of the transducer increases for any reason (see FIG. 7b) such intersection may still occur so that the ringing 110 is selected as an echo, producing a spurious result. On the other hand, if the ringing level decreases, the wanted echo 108 may again be missed, as in FIG. 7c, and a spurious echo 112 detected in its stead. In the present system, on the other hand, these problems can be overcome, as may be illustrated by reference to FIGS. 8a–8c. In FIG. 8a, a first shot is taken using an initial short transmitted pulse 200, and in one advantageous embodiment of the invention, no blanking is utilized. Instead of blanking, a similar effect is achieved by allowing a receiver associated with the transducer to saturate during the transmit pulse. The saturation level 202 of the receiver can then determine the start level of the reference curve, if such is utilized, although in many cases detection of an echo 204 in the first portion of the received signal 206 may be adequately achieved merely by examining this portion for any upturn in the amplitude of the received signal, on the premise that the amplitude of ringing will be dropping sufficiently rapidly over the first portion of the curve that only a wanted echo will have sufficient amplitude to reverse the falling trend. Any change in the amplitude of ringing will neither change the saturation level nor significantly affect the validity of the premise; thus in FIG. 8b the level of ringing has increased, but the wanted echo can still be detected. In some cases, for example where a very strong spurious echo occurs in the first portion of the received signal, some alternative echo identification technique may be necessary; for example blanking of some form may be necessary to eliminate the unwanted echo. If blanking is used, the echo search simply begins at the point in the profile where the blanking would end, the echo profile itself remaining unblanked.

Once the initial portion of the received signal has been tested for the presence of a wanted echo, the shot sequence is complete if a wanted echo has been detected. If no wanted echo has been detected, a second shot is taken using a wider transmit pulse, a first portion of the received signal is blanked, and the remainder tested for a wanted echo. Since a first portion of the signal has already been tested for a wanted echo, all or most of this portion may be blanked over an interval 208, thus ensuring that ringing of the transducer has been considerably attenuated even at the commencement of the portion of the signal being tested. This facilitates choice of a suitable starting point for a reference curve 210 (see FIG. 8c) utilized to select a wanted echo 204.

The exemplary signal processing procedure SHOT shown in FIG. 6, the code portion of which is included in the Appendix, will now be described in more detail, using the labels included in the Appendix and where appropriate in FIG. 6. Various subroutines called by the code listed in the Appendix and not directly relevant to the invention will not be discussed.

By calling a subroutine CRES, the size of sample file or data base to be formed from the received signal is calculated, based upon the range span (P3) and resolution (P1) required. The P designations refer to parameters stored in NOVRAM or RAM and are fetched utilizing the subroutine RCL. A test is then made of whether the blanking interval 208 is greater or less than 5.76 ms, equivalent to a 1 meter range. If the answer is affirmative, a jump is made to SHOT 1, described later. Otherwise the subroutine ATTN (not listed in the Appendix) is called which turns on an attenuator in the receiver 26 to suit its response to strong echoes. Subsequently the subroutine FIRE (not listed) is called which causes the transmitter to fire a pulse, the duration of which is determined by a parameter (in this case 8) passed in register A of microprocessor 12, and the received signal to be digitized by converter 24. Since only a first portion of the received signal is of interest, only samples relating to this portion are stored in RAM by the subroutine fire.

The file F0 of stored information is then truncated by the subroutine GRASS to remove data when the signal level falls below 50 dB, and transferred to a further file F1 by the subroutine COMP, where it is processed by the subroutine RECH to select the first echo with a rising edge greater than an amount set by parameter P75, and to return in various registers the elapsed time to the echo and various parameters of the echo, and the confidence level (CONF) that a wanted echo has been detected. The confidence level in this instance is considered to be the height of the rising edge of the echo, provided that the echo peak has a predetermined minimum amplitude and the elapsed time corresponds to a range less than 1 meter, failing which a confidence level of zero is returned, indicating failure to detect a wanted echo. A test is then made to determine whether a suitable echo, was found, failing which execution jumps to subroutine SHOT 1. If an echo was detected, execution jumps to label SHOT 2, discussed further below.

In the routine SHOT 1, the subroutine ATTN is again called, but with a different parameter so as to disable the receiver attenuator since the signals of interest will be at a lower level. The subroutine FIRE is called, also with passage to a different parameter (40) corresponding to a much longer transmit pulse, in this example five times longer than the short pulse, and an extended range of samples corresponding to the full required span is stored in file F0 by subroutine fire. The stored data is then filtered by the subroutine NSPK to remove spikes and interference from the data which are of too short a duration to represent valid echoes, and transferred to file F1 by subroutine COMP. A reference curve is then formed in file F2 utilizing the data from file F1 to determine a start point and then form a smoothed curve from which echo information has been filtered by forming running averages of groups of successive samples. File F1 is then reloaded with the data from file F0, and a first portion of the data is blanked by subroutine BLANK, whereafter the reference curve is then shifted upwardly by a subroutine AHVL so that it intersects the largest echo at midpoint. Thereafter a subroutine FECH selects the earliest echo of sufficient amplitude extending above the reference curve, returning similar data in the same registers as those used by the subroutine RECH. In this context, "sufficient amplitude" may be some fraction, typically half, of the amplitude of the largest echo. In this instance the confidence level CONF is considered to be the difference between the selected echo and the next largest echo. If no valid echo is detected, the confidence level is zero. Execution then reaches label SHOT 2.

At label SHOT 2, a subroutine AGIT is called which stores the echo parameters passed by the subroutine RECH or FECH, and tests the validity of the data. If the confidence level is zero, then previous echo data is retained, and the stored confidence level is set to zero. Otherwise, the echo position (PEAK PNTER) is tested against a window containing a previously stored echo position (or such a window is formed if necessary from the new echo), and parameters P63 (confidence level), P64 (echo position), P86 (window duration) and P87 (window starting point) are updated in RAM if necessary. The echo time delay is then calculated by subroutine ETD and stored as parameter P93 to complete the routine.

According to the confidence level obtained and other factors, the SHOT routine may then be repeated if necessary, as set forth in U.S. Pat. No. 4,596,144.

It will be understood that the hardware and routines described are exemplary only of those that may be utilized to implement the invention as set forth in the appended claims.

For example, the routine SHOT 1 may advantageously be utilized with a medium length transmitted pulse, even without the preceding use of a short pulse if rapid operation is important. The SHOT 1 routine is particularly useful in isolating valid echoes in liquid level measurements in tanks where reflections may occur between the liquid and the top of the tank. Furthermore, even if the short pulse routine produces an apparently valid echo, the SHOT 1 routine could be utilized, and if that too produces an apparently valid echo, then a determination could be made as to which was the true echo. This technique may be useful when structural features of the enclosure being monitored tend to result in spurious short range echoes.

I claim:

1. A unit providing at least one monitoring function for an industrial installation comprising an environmentally sealed casing, said casing having sealed window means providing the sole direct user interface to the unit, and containing a computer comprising a microprocessor, a read only memory accessible by the microprocessor and containing a stored program dedicating the microprocessor to at least one predetermined monitoring function, a human readable visual data display device within the casing and visible through said window means, a radiation transducer within the casing and responsive to data modulated radiation of a type to which at least part of the casing is transparent, at least one first peripheral interface element and second and third peripheral interface elements, said first, second and third peripheral interface elements interfacing the microprocessor respectively to connections for at least one monitoring transducer external of the casing and associated with said installation, to said data display device, and to said radiation transducer, a first random access memory accessible to the microprocessor and providing working memory and temporary data storage therefor, a second non-volatile random access memory accessible to the microprocessor and providing storage for data relating to normally constant parameters of said at least one monitoring function, said stored program consisting of a first normally active portion configuring the computer to carry out the at least one monitoring function of the unit, said portion accessing said second memory only for the reading of said normally constant parameters from defined locations therein, and a second normally inactive portion operative to decode signals received from the radiation transducer by the third peripheral interface unit to recover data representing said normally constant parameters, and to store said data in said defined locations in said second memory responsive to said signals, the third peripheral interface element including means responsive to receipt of signals from the radiation transducer to activate said second program portion; said unit further including a portable keypad comprising plural keys and means including a radiation source to generate data modulated radiation according to which of said plural keys is depressed, the casing including a dock to receive said unit with said radiation source in alignment with and adjacent said radiation transducer.

2. A unit according to claim 1, wherein the dock is a recess in a transparent lid of the casing, said recess being shaped to receive a rear casing of the keypad opposite the keypad, the radiation source is adjacent a window in said rear casing, and the radiation transducer is mounted within the casing behind the recess.

3. A unit according to claim 2, wherein the rear casing of the keypad comprises ferromagnetic material, and magnets are secured within the recess to detain the keypad therein.

4. A unit according to claim 1, wherein the means responsive to receipt of signals from the radiation transducer is responsive only to a signal representing a specific key, and the second program portion includes a routine responsive to a signal representing a specific key to deactivate said second program portion and re-activate said first program portion.

5. A unit according to claim 1, wherein the monitoring transducer is a sonic transducer of an acoustic ranging system which transmits pulses of sound energy and receives reflected energy in the form of echoes from a surface whose distance is to be determined, wherein the first program portion executes a program loop which contains a shot routine which causes the transmission of a pulse, the reception of reflected energy, the identification of echoes, and the calculation of echo parameters, and wherein the second program portion sets the parameters utilized by the first program portion in performing its functions.

6. A unit according to claim 5, wherein the second program includes a test routine selectable by signals from the keypad which returns to the main program portion for a single execution of the shot routine and then returns to the second program portion to display an echo parameter, and wherein one of the echo parameters determined by the shot routine is indicative of the degree of confidence that the correct echo has been determined and it is this parameter that is displayed, whereby by repeated selection of the test routine the effect of transducer adjustments may be assessed.

* * * * *